(12) United States Patent
Raab et al.

(10) Patent No.: US 9,289,560 B2
(45) Date of Patent: Mar. 22, 2016

(54) DRIVE ASSEMBLY FOR A DRUG DELIVERY DEVICE AND DRUG DELIVERY DEVICE

(75) Inventors: Steffen Raab, Frankfurt am Main (DE); Uwe Dasbach, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 734 days.

(21) Appl. No.: 13/509,601

(22) PCT Filed: Dec. 6, 2010

(86) PCT No.: PCT/EP2010/068915
§ 371 (c)(1),
(2), (4) Date: Nov. 27, 2012

(87) PCT Pub. No.: WO2011/069935
PCT Pub. Date: Jun. 16, 2011

(65) Prior Publication Data
US 2013/0110054 A1 May 2, 2013

(30) Foreign Application Priority Data

Dec. 7, 2009 (EP) ..................................... 09178213

(51) Int. Cl.
*A61M 5/315* (2006.01)
*A61M 5/31* (2006.01)

(52) U.S. Cl.
CPC .......... *A61M 5/31586* (2013.01); *A61M 5/3146* (2013.01); *A61M 5/3156* (2013.01); *A61M 5/31541* (2013.01); *A61M 5/31555* (2013.01); *A61M 5/31573* (2013.01); *A61M 5/31585* (2013.01); *A61M 5/31593* (2013.01);
(Continued)

(58) Field of Classification Search
CPC .......... A61M 5/3146; A61M 5/31501; A61M 5/31541; A61M 5/31555; A61M 5/31556; A61M 5/3156; A61M 5/31573; A61M 5/31575; A61M 5/31585; A61M 5/31586; A61M 5/31593
See application file for complete search history.

(56) References Cited

U.S. PATENT DOCUMENTS

| 4,475,905 A | 10/1984 | Himmelstrup |
| 2012/0010575 A1* | 1/2012 | Jones et al. ................... 604/211 |

FOREIGN PATENT DOCUMENTS

| EP | 0611035 | 8/1994 |
| EP | 2292286 | 3/2011 |

(Continued)

OTHER PUBLICATIONS

International Preliminary Report on Patentability for Int. App. No. PCT/EP2010/068915, mailed Jun. 21, 2012.
(Continued)

*Primary Examiner* — Imani Hayman
(74) *Attorney, Agent, or Firm* — McDonnell Boehnen Hulbert & Berghoff LLP

(57) ABSTRACT

A drive assembly for a drug delivery device, comprising a housing with a proximal end and a distal end, and a longitudinal axis (A) extending between the proximal end and the distal end, a rotation sleeve being rotatable relative to the housing, and a piston rod being axially moveable relative to the housing. The piston rod is in mechanical cooperation with the rotation sleeve to be rotatable and moveable in the distal direction relative to the housing when the rotation sleeve rotates in a first direction (D1) and to be stationary in axial direction relative to the housing when the rotation sleeve rotates in a second direction (D2) opposite to the first direction (D1).

13 Claims, 5 Drawing Sheets

(52) U.S. Cl.
CPC ........ *A61M5/31501* (2013.01); *A61M 5/31556* (2013.01); *A61M 5/31575* (2013.01)

(56) References Cited

FOREIGN PATENT DOCUMENTS

| | | |
|---|---|---|
| JP | 2002-541931 A | 12/2002 |
| WO | 93/07922 | 4/1993 |
| WO | 99/38554 | 8/1999 |
| WO | 00/62847 | 10/2000 |
| WO | 2006/037434 | 4/2006 |
| WO | 2008/058665 | 5/2008 |
| WO | 2008/148864 | 12/2008 |
| WO | 2009/080775 | 7/2009 |
| WO | 2009/141067 | 11/2009 |
| WO | 2010/066796 | 6/2010 |
| WO | 2010/139630 | 12/2010 |

OTHER PUBLICATIONS

International Search Report for International App. No. PCT/EP2010/068915, completed Jun. 10, 2011.
Office Action for Japanese Patent Application No. 2012-542482, mailed Jun. 9, 2015.

* cited by examiner

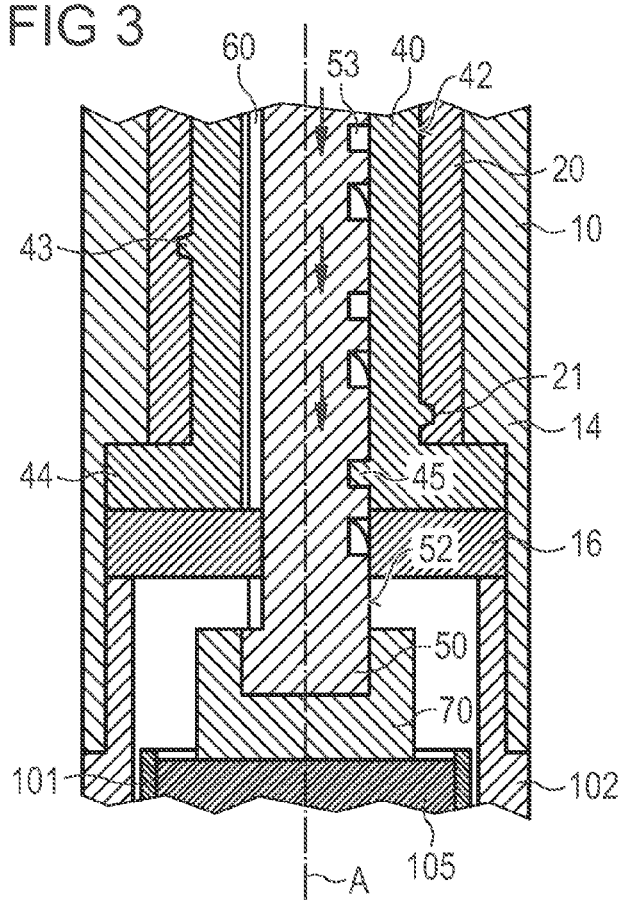
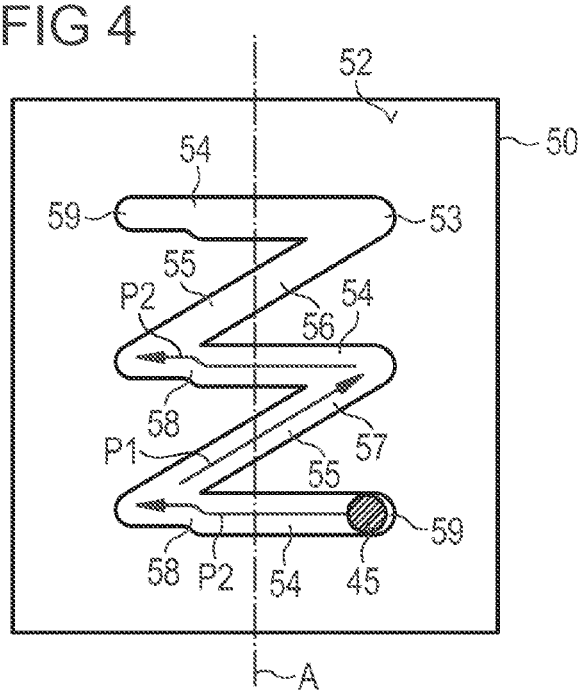

DRIVE ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2010/068915 filed Dec. 6, 2010, which claims priority to European Patent Application No. 09178213.6 filed on Dec. 7, 2009. The entire disclosure contents of these applications are herewith incorporated by reference into the present application.

FIELD OF INVENTION

The present invention relates to a drive assembly suitable for a drug delivery device and a drug delivery device.

BACKGROUND

Such drug delivery devices may have an application where a user without a formal medical training needs to administer an accurate and predefined dose of a medication or drug. In particular, such devices may have an application where medication is administered on a regular or an irregular base over a short term or long term period.

SUMMARY

It is an object of the invention to provide a drive assembly which provides improved operability. It is a further object of the invention to provide a drug delivery device which is simple to use and enables a precise delivery of the drug.

This object is achieved by a drive assembly according to claim 1 and a drug delivery device according to claim 15. Advantageous embodiments are subject matter of the dependent claims.

According to a first aspect, a drive assembly suitable for a drug delivery device comprises a housing. The housing comprises a proximal end and a distal end. A longitudinal axis extends between the proximal end and the distal end. The drive assembly further comprises a rotation sleeve. The rotation sleeve is rotatable relative to the housing. The drive assembly comprises a piston rod. The piston rod is axially moveable relative to the housing. The piston rod is in mechanical cooperation, e.g. in engagement, with the rotation sleeve to be moveable in the distal direction relative to the housing when the rotation sleeve rotates in a first direction relative to the housing, e.g. for delivering a dose of medication. The piston rod is in mechanical cooperation with the rotation sleeve to be stationary or essentially stationary in axial direction relative to the housing when the rotation sleeve rotates in a second direction opposite to the first direction, e.g. for setting or selecting a dose of medication. An axial movement may be a movement along the longitudinal axis of the housing.

The advantage of this drive assembly is that due to the axial movement of the piston rod relative to the housing a very high mechanical stability of the piston rod relative to the rotation sleeve can be achieved. Consequently, a very high mechanical stability of the drive assembly can be achieved.

The rotation sleeve may be secured against axial displacement with respect to the housing. The piston rod may be secured against rotational movement with respect to the housing.

In an advantageous embodiment a drive member is axially moveable relative to the housing. The drive member may be part of the drive assembly. The rotation sleeve is in mechanical cooperation, e.g. in engagement, with the drive member to be rotatable relative to the housing when the drive member is displaced in the axial direction relative to the rotation sleeve.

The rotation sleeve is arranged to be rotatable relative to the housing when the drive member is displaced in the distal direction or in the proximal direction by mechanical interaction of the drive member and the rotation sleeve. Preferably, the drive member is guided axially. The drive member may be splined to the housing. An axial force exerted on the drive member, for example by a user, is transformed into a rotational movement of the rotation sleeve with respect to the housing. That force can be transformed into a distal movement of the piston rod with respect to the housing when the rotation sleeve is rotating in the first direction.

This has the advantage that a simple transformation of an axial force on the drive member into a rotational movement of the rotation sleeve with respect to the housing is possible. Furthermore, the axial movement of the drive member may be controlled in a very precise manner. Therefore, an exact dosing of the medication is facilitated. Furthermore, this may be very convenient for the user of the drug delivery device as there is no rotational movement of the drive member necessary during its operation.

In a further advantageous embodiment the rotation sleeve rotates in the first direction relative to the housing when the drive member is displaced in the distal direction, and rotates in the second direction when the drive member is displaced in the proximal direction.

This has the advantage that a selection of a dose of the drug may be carried out in a simple manner when the drive member is displaced in the proximal direction. Furthermore, the delivery of the drug may be carried out in a simple manner when the drive member is displaced in the distal direction. Furthermore, the axial movement of the drive member allows controlling the selection of the dose as well as the injection of the dose very simply. Therefore, a very exact dosing of the medication with a very low risk of application of a wrong dose is facilitated.

In a further advantageous embodiment the drive member and the rotation sleeve are in engagement by a thread. Preferably, the drive member has an inner thread which engages with an engaging device of the rotation sleeve. Alternatively, the rotation sleeve may have an outer thread which engages with an engaging device of the drive member.

The thread is a suitable means to couple the drive member and the rotation sleeve for a transformation of the axial movement of the drive member into a rotational movement of the rotation sleeve with respect to the housing.

According to a further advantageous embodiment the rotation sleeve comprises a radial protrusion. The protrusion is arranged in axial direction between two sections of the housing. The two sections prevent an axial movement of the rotation sleeve.

This has the advantage that an axial movement of the rotation sleeve can be prevented in a simple way, and only a rotational movement of the rotation sleeve is possible.

According to a further advantageous embodiment the piston rod has an outer surface provided with at least one guide track arranged on the outer surface. The rotation sleeve comprises a guide piece which is disposed and movable in the guide track.

Preferably, one guide track is arranged on the outer surface of the piston rod.

This has the advantage that the guide track and the guide piece can be simply designed to cooperate as a slotted guide which has very good mechanical coupling characteristics.

According to a further embodiment the guide track forms a zigzag-like line on the outer surface of the piston rod. The zigzag-like line extends in axial direction.

This has the advantage that the piston rod is moveable in the distal direction relative to the housing when the rotation sleeve is rotating in the first direction and is stationary in axial direction relative to the housing when the rotation sleeve is rotating in the second direction opposite to the first direction to the housing.

According to a further advantageous embodiment the guide track comprises first sections and second sections. The first sections are perpendicular relative to the longitudinal axis. The second sections are oblique relative to the longitudinal axis.

This has the advantage that the piston rod is moveable in the distal direction relative to the housing when the rotation sleeve is rotating in the first direction and is stationary in axial direction relative to the housing when the rotation sleeve is rotating in the second direction opposing the first direction to the housing.

According to a further advantageous embodiment the first sections are designed to prevent an axial movement of the piston rod. The first sections may have an extension perpendicular relative to the longitudinal axis which limits the rotational angular movement of the rotation sleeve. In particular, rotational movement of the rotation sleeve in the second direction with respect to the piston rod may be limited by the angular extension of the first sections.

According to a further advantageous embodiment the second sections are designed to convert rotational movement of the rotation sleeve in the first direction into axial movement of the piston rod, for example by mechanical interaction of the rotation sleeve and the piston rod in the second sections.

In a further advantageous embodiment the guide track comprises at least one priming section. The priming section is arranged between one of the first sections and one of the second sections.

This has the advantage that a priming operation can be carried out after the selection of the dose has been commenced and before the dispensing of the medication is initiated. This facilitates an exact mechanical alignment between different parts of the drug delivery device and, consequently, may increase dose accuracy.

In a further advantageous embodiment the guide track comprises at least one end section. The at least one end section is designed to limit the axial movement of the piston rod.

This has the advantage that a further distal movement of the piston rod can be prevented.

In a further advantageous embodiment the piston rod is splined to the housing.

This has the advantage that the movement of the piston rod in axial direction can be carried out in a very exact manner.

According to a second aspect a drive assembly suitable for a drug delivery device comprises a housing. The housing comprises a proximal end and a distal end. A longitudinal axis extends between the proximal end and the distal end. The drive assembly further comprises a rotation sleeve. The rotation sleeve is rotatable relative to the housing. The drive assembly comprises a piston rod. The piston rod is axially moveable relative to the housing.

The piston rod has an outer surface with a guide track arranged on the outer surface. The rotation sleeve comprises a guide piece which is disposed and which is movable in the guide track. The guide track and the guide piece are designed to cooperate as a slotted guide.

This has the advantage that the guide track and the guide piece can be simply designed to cooperate as a slotted guide which allows a good guiding of the piston rod relative to the rotation sleeve.

According to a third aspect a drug delivery device comprises a drive assembly. The drug delivery device comprises a medication containing cartridge. The piston rod interacts with a bung which is arranged in the medication containing cartridge to dispense the medication.

The terms "medication", "medicament" and "drug" are used as equivalent expressions in this context.

The terms "medication", "medicament" and "drug", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2,
des Pro36[Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17.ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Exemplary embodiments of the invention are explained in the following with the help of schematic drawings. These are as follows.

DETAILED DESCRIPTION

Figure 1:
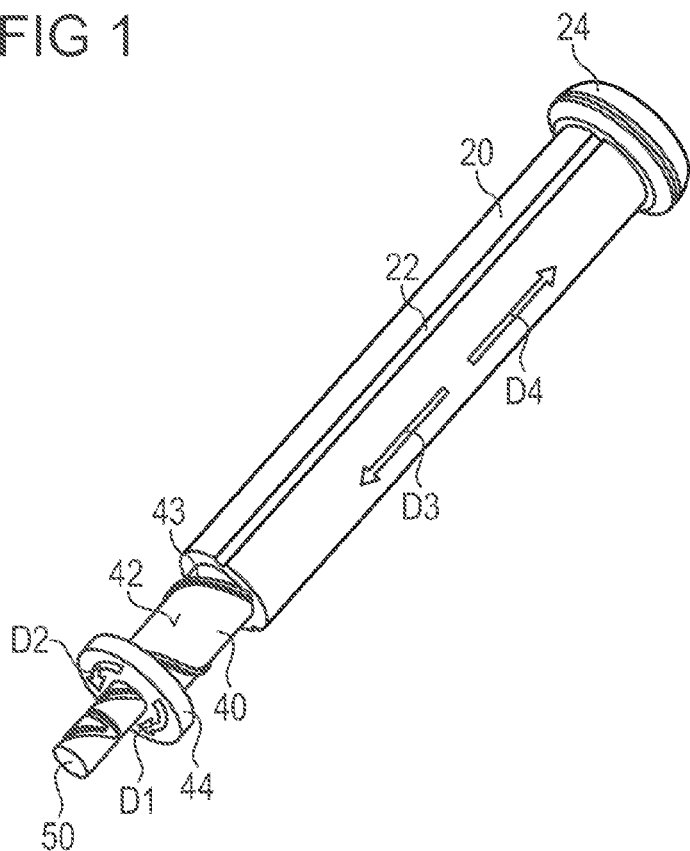
FIG. 1 schematically shows parts of a drive assembly according to an embodiment in a perspective view, FIG. 2 schematically shows a drive member, a rotation sleeve and a piston rod of the drive assembly according to an embodiment in a perspective view, FIG. 3 schematically shows a section of the drug delivery device with the drive assembly according to an embodiment in a longitudinal section view, FIG. 4 schematically shows a section of the piston rod according to an embodiment in a plan side view, FIG. 4A schematically shows a section of the piston rod according to a further embodiment in a plan side view, FIG. 4B schematically shows a section of the piston rod according to a further embodiment in a plan side view, FIG. 4C schematically shows a section of the piston rod according to a further embodiment in a plan side view, FIG. 4D schematically shows a section of the piston rod according to a further embodiment in a plan side view, and FIG. 5 schematically shows a drug delivery device.
Figure 2:
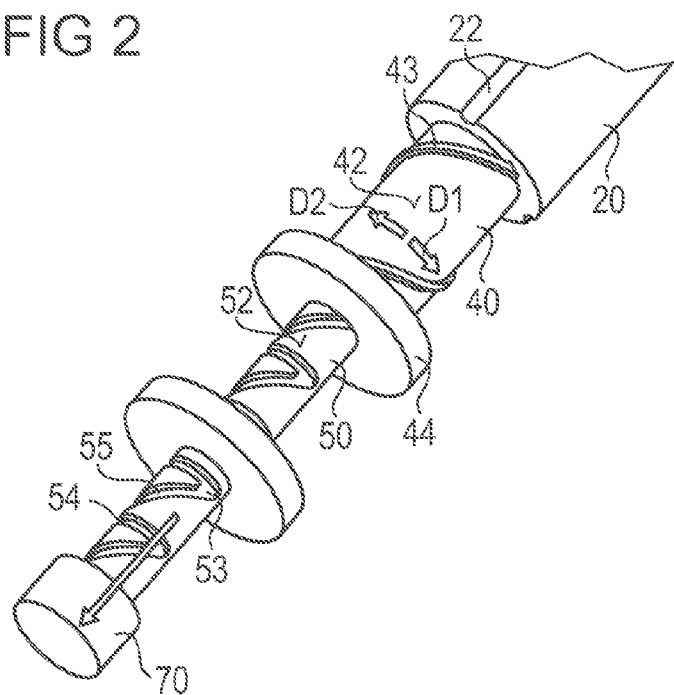

FIGS. 1 and 2 show a drive assembly. The drive assembly is preferably part of a drug delivery device 100 (see FIG. 5). Preferably, the drug delivery device 100 is a pen-type drug delivery device which may inject drugs. Preferably, the drug delivery device 100 is a fixed dose device which is configured to dispense pre-set doses. The drive assembly comprises a housing 10 (see FIGS. 3 and 5). Furthermore, the drive assembly comprises a drive member 20 and a rotation sleeve 40. Additionally, the drive assembly comprises a piston rod 50.

Preferably, the housing 10 extends between a proximal end 11 and a distal end 12. The housing 10 may have a hollow cylindrical shape. Preferably, the housing 10 comprises a first section 14 and a second section 16. The first section 14 is shaped like a sleeve. The second section 16 is shaped like a disk. The second section 16 is fixedly coupled to the first section 14.

Figure 5:
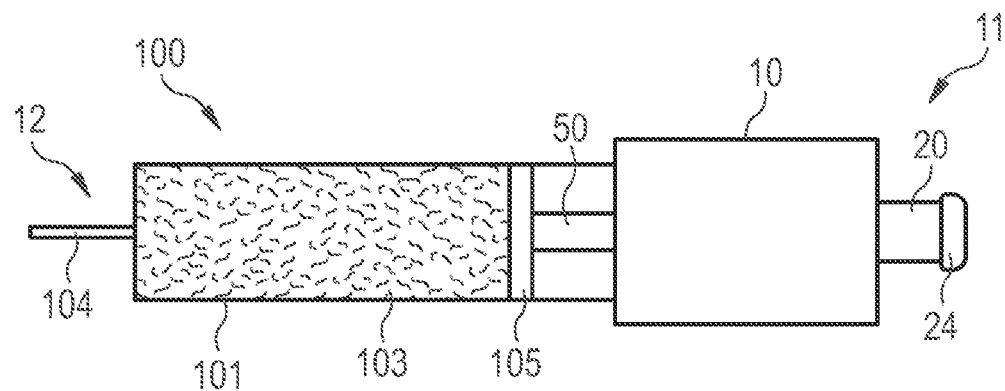

The housing 10 may comprise coupling means on the distal end 12. The housing 10 may comprise coupling means arranged at the distal end 12. The coupling means on the distal end 12 may be for coupling the housing 10 with a cartridge holder 102 (FIG. 5). The cartridge holder 102 interacts with the second section 16. The second section 16 acts as an intermediate element for the cartridge holder 102 to obtain a defined position of the cartridge holder 102.

A longitudinal axis A extends between the proximal end 11 and the distal end 12. The longitudinal axis A basically extends through the center of the housing 10. The surfaces of the housing 10 basically extend along the longitudinal axis A. The housing 10 may comprise an opening, for example to provide a display which may show the number of dispensed or remaining doses of drug.

The drive member 20 preferably comprises an inner thread 21 which is extending in axial direction (FIG. 3). The inner thread 21 of the drive member 20 follows a helical path with a centre axis of this path being the longitudinal axis A or an axis parallel to the longitudinal axis A. In alternative embodiments, the rotation sleeve 40 has an outer thread which engages with an engaging device of the drive member 20. The drive member 20 is axially displaceable with respect to the housing 10 and thereby enables a rotational movement of the rotation sleeve 40 via the thread 21. Preferably, any axial movement of the drive member 20 relative to the rotation sleeve 40 is converted into a rotational movement of the rotation sleeve 40.

The drive member 20 is preferably splined to the housing 10. The drive member 20 preferably comprises at least one groove 22 which is extending in axial direction. The groove 22 is in engagement with the housing 10 for example with a tab. The tab is a part of the housing 10 or is locked to the housing 10. The groove 22 being in engagement with the housing 10 can ensure an axial movement of the drive member 20 relative to the housing 10. In alternative embodiments, the housing 10 comprises a groove and the drive member 20 has a tab being in engagement with the groove.

The drive member 20 preferably comprises coupling means for coupling the drive member 20 with further elements. For example, a dose button 24 is coupled to the drive member 20. The dose button 24 may transfer a force exerted on the dose button 24 in distal or proximal direction to the drive member 20. The dose button 24 may be pushed in the distal direction with respect to the housing 10 for administering a dose of medication. The dose button 24 may be pulled in the proximal direction with respect to the housing 10 for setting a dose of medication. In another embodiment the force for administering a dose of medication is exerted directly on the drive member 20. In this embodiment no separate dose button 24 is needed. The force may be a force being exerted manually on the dose button 24 by a user.

The rotation sleeve 40 has an outer surface 42. The outer surface 42 comprises an engaging device 43 which extends in axial direction and is in engagement with the thread 21 of the drive member 20. The thread 21 and the engaging device 43 enable a transformation of an axial movement of the drive member 20 into a rotational movement of the rotation sleeve 40. A rotational movement of the rotation sleeve 40 can be carried out in a first direction D1 or in a second direction D2 which is counterclockwise to the first direction D1. In particular, a rotational movement of the rotation sleeve 40 in the first direction D1 can be achieved by a movement of the drive member 20 in a distal direction D3 relative to the housing 10 which is a distal movement of the drive member 20. Accordingly, a rotational movement of the rotation sleeve 40 in the second direction D2 can be achieved by an axial proximal movement of the drive member 20 relative to the housing 10 in a proximal direction D4.

The rotation sleeve 40 further comprises a protrusion 44, e.g. a radially outwardly directed flange, extending in radial direction. As the protrusion 44 is arranged in axial direction between the first section 14 and the second section 16 of the housing 10 (see FIG. 3) an axial movement of the rotation sleeve 40 relative to the housing 10 can be prevented. Therefore, the rotation sleeve 40 carries out a rotational movement in the first direction D1 and in the second direction D2 only.

The rotation sleeve 40 has a guide piece 45 protruding from an inner surface of the rotation sleeve 40 in radial direction, in particular towards the longitudinal axis A of the housing 10. The guide piece 45 is in engagement with the piston rod 50.

The piston rod 50 has an outer surface 52. A guide track 53 is arranged on the outer surface 52 of the piston rod 50. Preferably, the guide piece 45 of the rotation sleeve 40 is arranged in the guide track 53. Preferably, the guide piece 45 is moveable in the guide track 53. The engagement of the guide piece 45 and the guide track 53 enables a secure connecting link between the rotation sleeve 40 and the piston rod 50.

Figure 4A:
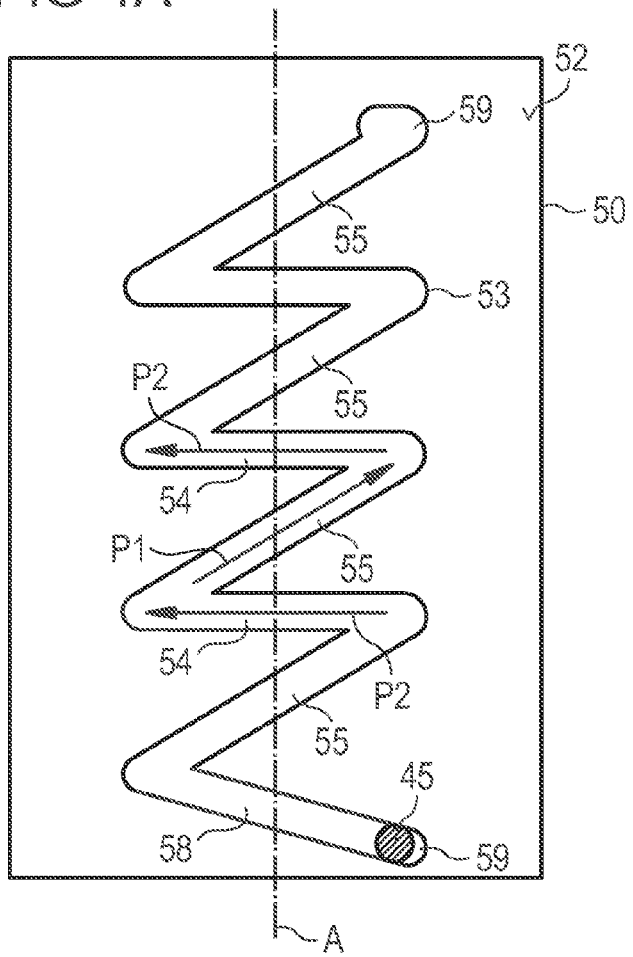

Preferably, the guide piece 45 has a circular square section, as shown in FIGS. 4 and 4A. This allows a smooth and secure movement of the guide piece 45 in the guide track 53.

FIG. 4 shows in a detailed view the guide track 53 of the piston rod 50. The guide piece 45 and the guide track 53 are engaged. The guide track 53 runs on the outer surface 52 of the piston rod 50 which may be curved. For illustrating the function of the rotation sleeve 40 and the piston rod 50 the path of the guide track 53 is shown in plan view in FIG. 4. The guide track 53 may be moved along the guide piece 45 when the piston rod 50 is moved in the distal direction.

Figure 4B:
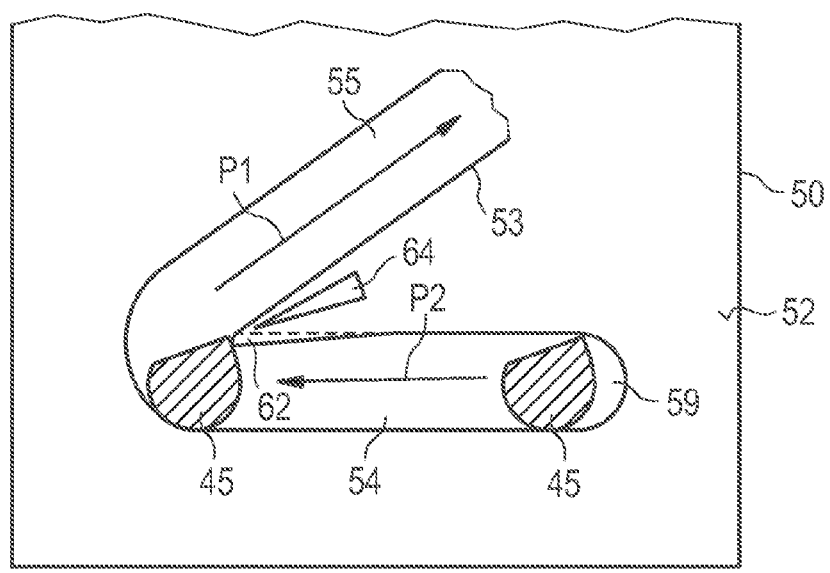

As can be seen particularly in FIGS. 4, 4A and 4B, the guide track 53 is preferably formed as a zigzag-like line on the outer surface 52 of the piston rod 50. Preferably, the zigzag-like line forming the guide track 53 is extending in axial direction, in particular as far as a main direction of extent of the guide track 53 is concerned.

Figure 4C:
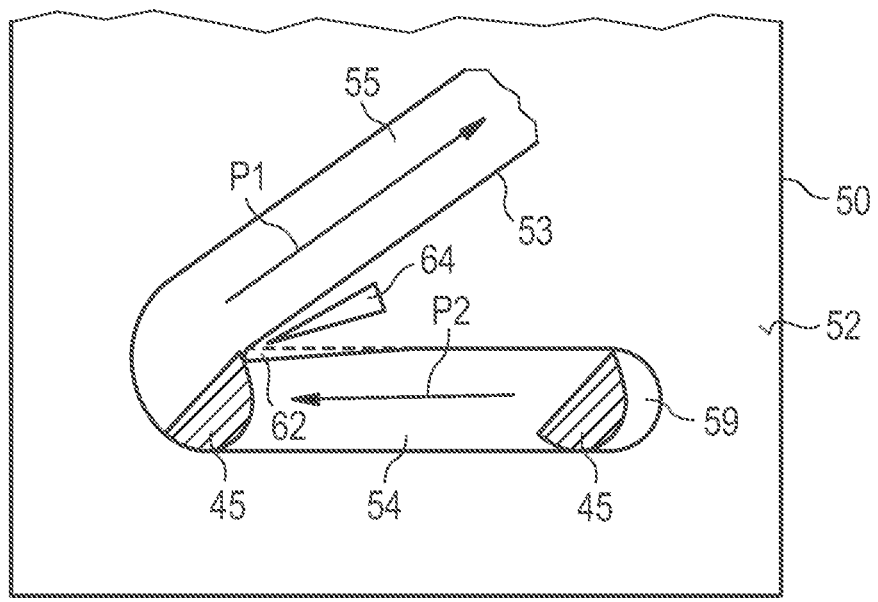
Figure 4D:
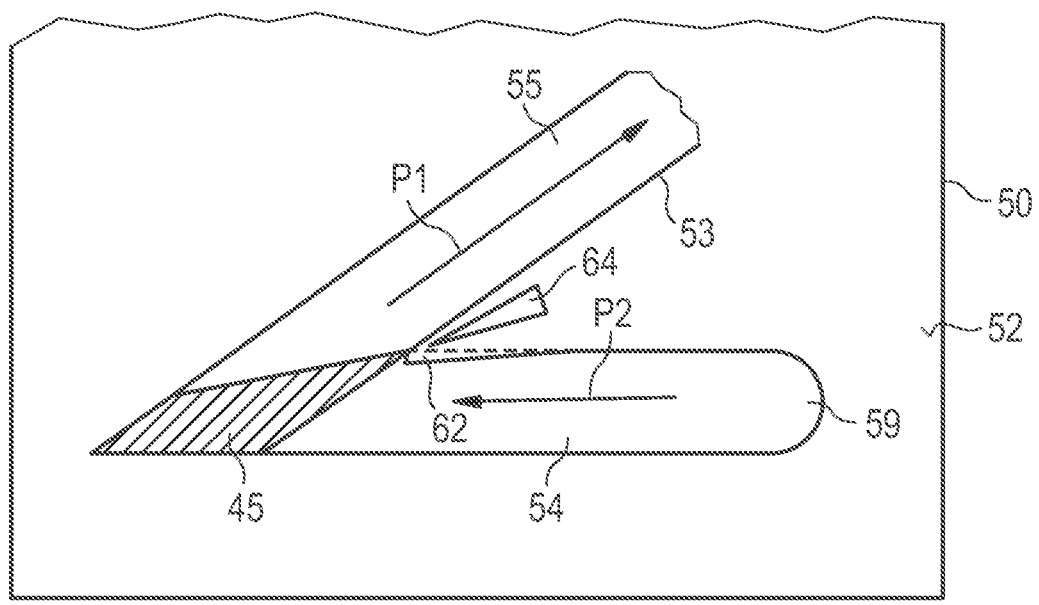

The guide track 53 has consecutive segments, and each of the consecutive segments of the guide track 53 comprises a first section 54 and a second section 55. Each of the consecutive segments of one of the first sections 54 and one of the second sections 55 is formed as a "V". A single of these consecutive segments formed as a "V" is shown in FIG. 4B, 4C and 4D. The first sections 54 extend expediently perpendicular or essentially perpendicular relative to the longitudinal axis A and are acting as dose setting sections. The guide piece 45 travels in the first sections 54 during dose setting. The second sections 55 extend obliquely relative to the longitudinal axis A and are acting as dose dispensing sections. If the first section 54 of a segment is oblique with respect to the axis A, the second section 55 of that segment is preferably more oblique with respect to the axis A. It is, however, preferred that the first sections 54 extend perpendicular with respect to the axis A. The guide piece 45 travels in the second sections 55 during dose dispensing. The second sections 55 define first paths P1, and the first sections 54 define second paths P2. The first paths P1 and the second paths P2 are designed to guide the guide piece 45. In general, the first sections 54 and the second sections 55 are alternatingly disposed along the guide track 53 thereby forming the zigzag line for the guide track 53.

In an alternative embodiment, the guide track 53 has second sections 56, 57 with different axial extensions. The angle of one 56 of the second sections as seen in projection on the axis A may be different from the angle of the other 57 of the second sections as seen in projection on the axis A. Consequently, the length of the one 56 of the second sections may be different from the length of the other 57 of the second sections. As the axial extension of the oblique second section 55 defines the axial displacement of the piston rod 50, the length of the second sections 56, 57 determines the dose of drug injected during the traveling of the guide piece 45 on the second section 55.

In the embodiment of FIG. 4, between one end of the one of the first sections 54 and an adjacent end of one of the second sections 55 a priming section 58 is arranged. The priming section 58 enables a small axial movement of the guide track 53 with respect to the guide piece 45 during the transition of the guide piece 45 from an interaction with the first section 54 to an interaction with the second section 55. The small axial movement may be effected by converting the rotation of the rotation sleeve 40 in the first direction D1 into axial movement when the guide piece 45 interacts with the priming section 58. Due to the small axial movement, which may be small as compared to the axial movement of the piston rod 50 during dose delivery, the guide piece 45 and the guide track 53 may be positioned relative to each other such that the guide piece 45 may interact with the second section 55 of the current segment during a subsequent rotation of the rotation sleeve 40 in the second direction D2.

The guide track 53 further comprises two end sections 59, one at the upper end and one at the lower end of the guide track 53 with respect to FIGS. 4 and 4A.

The piston rod 50 furthermore comprises a guiding element 60. By this the piston rod 50 is splined to the housing 10. This facilitates a precise movement of the piston rod 50 in the axial direction without a rotation.

In the embodiment of FIG. 4A, the priming section 58 is arranged at the lower end of the guide track 53 and is shaped as an oblique section. The priming section 58 enables an axial movement of the guide track 53 with respect to the guide piece 45. This axial movement may be effected by converting the rotation of the rotation sleeve 40 in the first direction D1 into an axial movement when the guide piece 45 interacts with the priming section 58 prior to the first dose delivery. Due to this axial movement, which may be small compared with the axial movement of the piston rod 50 during dose delivery, the guide piece 45 and the guide track 53 may be positioned relative to each other such that the guide piece 45 may interact with the second section 55 of the current segment during a subsequent rotation of the rotation sleeve 40 in the second direction D2.

In the embodiment of FIG. 4A, the end section 59 is arranged directly at the proximal end of the uppermost second section 55 relative to FIG. 4A. This makes it possible to prevent already a further setting movement of the piston rod 50 immediately after the last allowed dose has been dispensed. In the embodiment of FIG. 4, a subsequent dose setting movement is allowed, whereas the subsequent dose dispensing movement which would have to be performed is prevented.

In the embodiment of FIGS. 4B and 4C the guide piece 45 has a quasi-circular square section with an oblique cut at its proximal end. The angles of the oblique cuts are different in FIGS. 4B and 4C. The oblique cut allows a smooth and secure movement of the guide piece 45 in the guide track 53.

In the embodiment of FIG. 4D the guide piece 45 has a quadrilateral square section. This shape of the guide piece 45 allows a secure movement of the guide piece 45 in the guide track 53.

Furthermore, in the embodiment of FIGS. 4B, 4C and 4D the first section 54 of the guide track 53 has a wedge-shaped projection 62 extending from the proximal wall of the first section 54. The projection 62 may be elastically deformable. The projection 62 reduces the cross section, in particular the axial extension of the first section 54. The first section 54 may taper in the direction from the right to the left in view of FIGS. 4B, 4C and 4D. The projection 62 is in mechanical cooperation with the guide piece 45. The shape of the guide piece 45 of FIGS. 4B, 4C and 4D in particular in combination with the wedge-shaped projection 62 may prevent an unintended backward movement of the guide piece 45 in the guide track 53. The reason for this is that after the guide piece 45 has passed the projection 62 during its movement from the first section 54 to the second section 55 the shape of the guide piece 45 with its upper right edge and the shape of the projection 62 result in that the guide piece 45 snaps into the second section 55 and therefore prevent a movement of the guide piece 45 from the second section 55 back to the first section 54.

Additionally or alternatively, in the embodiment of FIGS. 4B, 4C and 4D a recess 64 is arranged between the first section 54 and the second section 55 adjacent to the projection 62. The recess 64 increases the flexibility of the projection 62 in the case that the guide piece 45 passes the projection 62 during its movement from the first section 54 to the second section 55. Consequently, a reliable passing of the guide piece 45 from the first section 54 to the second section 55 is possible without an interference of the prevention of the movement of the guide piece 45 from the second section 55 back to the first section 54.

FIG. 5 shows the drug delivery device 100. The drug delivery device 100 may be a fixed dose device, in particular a device for dispensing fixed, non user-variable, for example constant, doses. The drug delivery device 100 comprises a medication containing cartridge 101 which is arranged in the cartridge holder 102 (FIG. 3). The cartridge 101 holds a medication 103. Medication and drug are used as equivalent expressions in this context. The drug delivery device 100 further comprises a needle device 104. The needle device 104 is arranged at the distal end of the medication containing cartridge 101 and is preferably secured to it. The medication 103 can be dispensed through the needle device 104. The medication 103 may comprise insulin, growth hormones, low molecular weight heparins, and/or their analogues and/or derivatives. The medication 103 may be a fluid.

A bung 105 is arranged inside the cartridge 101. The bung 105 is capable of being displaced inside the cartridge 101. A displacement of the bung 105 in the distal direction relative to the cartridge 101 results in a dispensing of medication. The movement of the bung 105 is actuated by the piston rod 50. The piston rod acts on the bung 105 via a bearing 70. Preferably, the bearing 70 is axially arranged between the piston rod 50 and the bung 105. Alternatively, the bearing 70 may be dispensed with.

At the proximal end of the medication containing cartridge 101, the drive assembly is arranged. The medication containing cartridge 101 is preferably secured to the housing 10 at the distal end side of the housing 10.

In the following, the function of the drive assembly and the drug delivery device will be described in detail in particular in view of the embodiment of FIG. 4:

An actuation of the dose button 24, preferably a manually actuated movement of the dose button 24 with respect to the housing 10, causes linear displacement of the drive member 20 which is part of the drive assembly. The drive member 20 is linearly displaced in the distal direction, for example towards the distal end 12, and the needle device 104 respectively. The linear displacement of the drive member 20 causes a rotational movement of the rotation sleeve 40 in one of the first or second directions D1, D2 and a corresponding displacement of the piston rod 50. The displacement of the piston rod 50 in the injection phase is preferably linear.

During a setting of the dose, the user pulls the drive member 20 in the proximal direction D4. As the movement of the drive member 20 in the proximal direction D4 relative to the housing 10 is correlated with a rotational movement of the rotation sleeve 40 in the second direction D2, the guide piece 45 of the rotation sleeve 40 travels along the first section 54 of the guide track 53 on the second path P2 from the right to the left with respect to FIG. 4. In a not shown further embodiment with a guide track in a mirror image arrangement with respect to FIG. 4 the guide piece may travel along the first section of the guide track from the left to the right on the second path. The movement of the guide piece 45 is restricted by two walls limiting the guide track 53. The guide piece 45 travels along the second path P2 until the guide piece 45 comes into contact with a wall of the guide track 53, e.g. a wall at the left of the guide track 53, near the transition area or in the transition area between the first section 54 and the second section 55 of the current segment of the guide track 53.

During the transition of the guide piece 45 from one of first sections 54 to one of the second sections 55 the guide piece 45 passes the priming section 58. By this a small axial movement of the piston rod 50 in distal direction is achieved. Beside this small axial movement of the piston rod 50 the piston rod 50 can not move in axial direction relative to the housing 2 during the dose setting process. The small axial movement of the piston rod 50 may achieve an exact mechanical alignment of the piston rod 50 relative to the housing 10 and the cartridge 101. Consequently, an exact dosing of the medication 103 during the following dispensing phase is facilitated. Furthermore, the priming section 58 may prevent a movement of the guide piece 45 along the second path P2 back to the starting point during the following process step as another wall, e.g. the wall at the right of the guide track 53, will mechanically cooperate with the guide piece 45 to prevent re-entering the previously passed first section 54. At the end of the second path P2 the dose setting process is completed.

For dispensing the dose, the user pushes the drive member 20 of the drug delivery device 100 in the distal direction D3. As the movement of the drive member 20 in the distal direction D3 relative to the housing 10 is correlated with a rotational movement of the rotation sleeve 40 in the first direction D1, the guide piece 45 of the rotation sleeve 40 follows the first path P1 of the second section 55 from the left to the right with respect to FIG. 4. The movement of the guide piece 45 is again restricted by the two walls limiting the guide track 53. The guide piece 45 now cooperates with the wall right of the guide track 53. Therefore, the guide piece 45 travels along the first path P1 until the guide piece 45 reaches the transition area between the second section 55 of the current segment and the first section 54 of a subsequent segment of the guide track 53. During this movement, the piston rod 50 is moved in distal direction due to the guide piece 45 interacting with the oblique wall of the second section 54. Thereby, medication 103 may be dispensed from the medication containing cartridge 101.

After a described cycle of setting and dispensing a dose has been carried out, a user may carry out the described steps of setting and dispensing a dose in consecutive steps, wherein the guide piece 45 of the rotation sleeve 40 is guided by the consecutive segment with one of the first sections 54 and one of the second sections 55. Thus, multiple doses of a medicament may be dispensed.

The end sections 59 of the guide track 53 limit the movement of the guide piece 45 and, consequently, the movement of the piston rod 50 relative to the housing 10. The two end sections 59 define the maximum number of consecutive sections and, consequently, dose setting and dose dispensing cycles which can be carried out by the user. In particular, the end section 59 at the proximal end of the guide track 53 can prevent a dispensing movement of the piston rod 50 after the last allowed dose has been dispensed.

The function of the drive assembly and the drug delivery device of the embodiment of FIG. 4A differ from the function of the embodiment of FIG. 4 as the priming section 58 is arranged at the lower end of the guide track 53 and is shaped as an oblique section. Therefore, the exact mechanical alignment of the piston rod 50 relative to the housing 10 and the cartridge 101 is carried out only once in connection with the first dose setting prior to the first dose dispensing so that an exact dosing of the medication 103 during the first dose dispensing phase can be obtained. Furthermore, the different position of the end section 59 at the proximal end of the guide track 53 can prevent a further setting movement of the piston rod 50 after the last allowed dose has been dispensed.

The function of the drive assembly and the drug delivery device of the embodiment of FIGS. 4B, 4C and 4D differs from the function of the embodiment of FIG. 4 in that the mechanical cooperation between the guide piece 45 and the wedge-shaped projection 62 may prevent a movement of the guide piece 45 along the second path P2 back to the starting point during the following process step. After the guide piece 45 has passed the wedge-shaped projection 62 the guide piece 45 snaps into the subsequent second section 55 and a re-entering into the previously passed first section 54 may be prevented by the wedge-shaped projection 62 blocking the passage from the second section 55 back into the first section 54.

The invention claimed is:

1. A drive assembly for a drug delivery device, comprising:
a housing with a proximal end and a distal end, and a longitudinal axis (A) extending between the proximal end and the distal end,
a rotation sleeve being rotatable relative to the housing,
a drive member is axially moveable relative to the housing, and
a piston rod being axially moveable relative to the housing, wherein the piston rod is in mechanical cooperation with the rotation sleeve to be moveable in the distal direction relative to the housing when the rotation sleeve rotates in a first direction (D1) and to be stationary in axial direction relative to the housing when the rotation sleeve rotates in a second direction (D2) opposite to the first direction (D1), wherein the rotation sleeve is in mechanical cooperation with the drive member to be rotatable relative to the housing when the drive member is displaced in axial direction relative to the rotation sleeve.

2. The drive assembly according to claim 1, wherein the rotation sleeve rotates in the first direction (D1) relative to the housing when the drive member is displaced in the distal direction, and rotates in the second direction (D2) when the drive member is displaced in the proximal direction.

3. The drive assembly according to claim 1, wherein the drive member and the rotation sleeve are in engagement by a thread.

4. The drive assembly according to claim 1, wherein the rotation sleeve comprises a radial protrusion being arranged in axial direction between two sections of the housing, the two sections preventing an axial movement of the rotation sleeve.

5. The drive assembly according to claim 1, wherein the piston rod has an outer surface provided with at least one guide track arranged on the outer surface, and the rotation sleeve comprises a guide piece being disposed and being movable in the guide track.

6. The drive assembly according to claim 5, wherein the guide track forms a zigzag-like line on the outer surface of the piston rod, the zigzag-like line essentially extending in axial direction.

7. The drive assembly according to claim 5, wherein the guide track comprises first sections and second sections, the first sections being perpendicular relative to the longitudinal axis (A) and the second sections being oblique relative to the longitudinal axis (A).

8. The drive assembly according to claim 7, wherein the first sections are designed to prevent an axial movement of the piston rod and have an extension perpendicular relative to the longitudinal axis (A) which limits the rotational movement of the rotation sleeve.

9. The drive assembly according to claim 7, wherein the second sections are designed to convert rotational movement of the rotation sleeve in the first direction into axial movement of the piston rod.

10. The drive assembly according to one of the claims 7 to 9, wherein the guide track comprises at least one priming section being arranged between one of the first sections and one of the second sections.

11. The drive assembly according to claim 5, wherein the guide track comprises at least one end section being designed to limit the axial movement of the piston rod.

12. The drive assembly according to claim 1, wherein the piston rod is splined to the housing.

13. A drug delivery device comprising the drive assembly according to claim 1, wherein the drug delivery device further comprises a medication containing cartridge and the piston rod interacts with a bung being arranged in the medication containing cartridge to dispense the medication.

* * * * *